United States Patent [19]

Levy et al.

[11] Patent Number: 5,436,291
[45] Date of Patent: Jul. 25, 1995

[54] CALCIFICATION-RESISTANT SYNTHETIC BIOMATERIALS

[75] Inventors: Robert J. Levy; Ravi Joshi, both of Ann Arbor, Mich.

[73] Assignee: University of Michigan, The Board of . . ., Ann Arbor, Mich.

[21] Appl. No.: 181,742

[22] Filed: Jan. 21, 1994

Related U.S. Application Data

[63] Continuation-in-part of PCT/US93/05601, Jul. 9, 1993, and a Continuation-in-part of Ser. No. 910,941, Jul. 9, 1992, Pat. No. 5,296,583.

[51] Int. Cl.$^6$ ............................................. C08G 18/10
[52] U.S. Cl. ................................. 524/706; 525/453; 528/59; 528/72; 528/73; 536/21; 514/56
[58] Field of Search .................. 524/706; 525/453; 528/59, 72, 73; 536/21; 514/56

[56] References Cited

U.S. PATENT DOCUMENTS 4,259,472  3/1981  Chatths et al. ..................... 528/72

*Primary Examiner*—Maurice J. Welsh
*Attorney, Agent, or Firm*—Rohm & Monsanto

[57] ABSTRACT

Synthetic biomaterials are provided with irreversibly bound amino diphosphonate, polyphosphonate, or other anticalcification agent to prevent in vivo calcification. Such biomaterials include biocompatible elastomers such as polyurethane and/or polydimethylsiloxane, and the like which are intended for invasive, or in-dwelling use in a human or animal body. Illustratively, reaction conditions utilizing hi-or polyfunctional epoxides result in epoxide bridge incorporation of the anticalcification agent to the biomaterial elastomer.

34 Claims, 11 Drawing Sheets

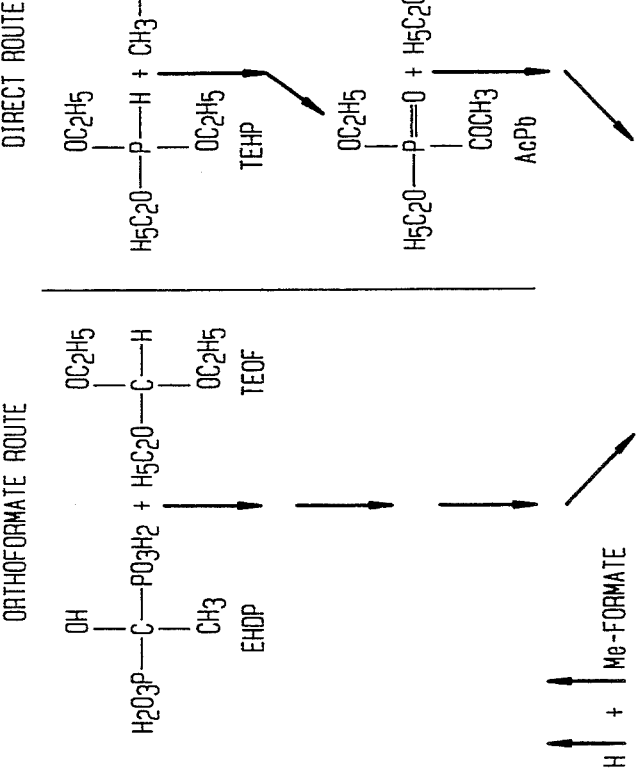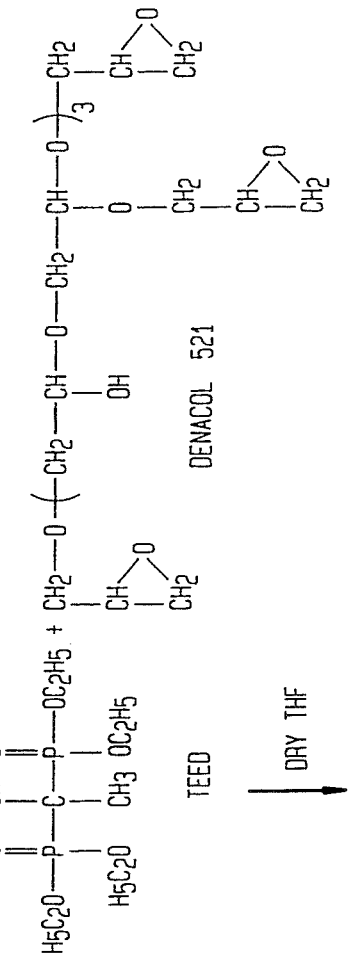
FIG. 5A

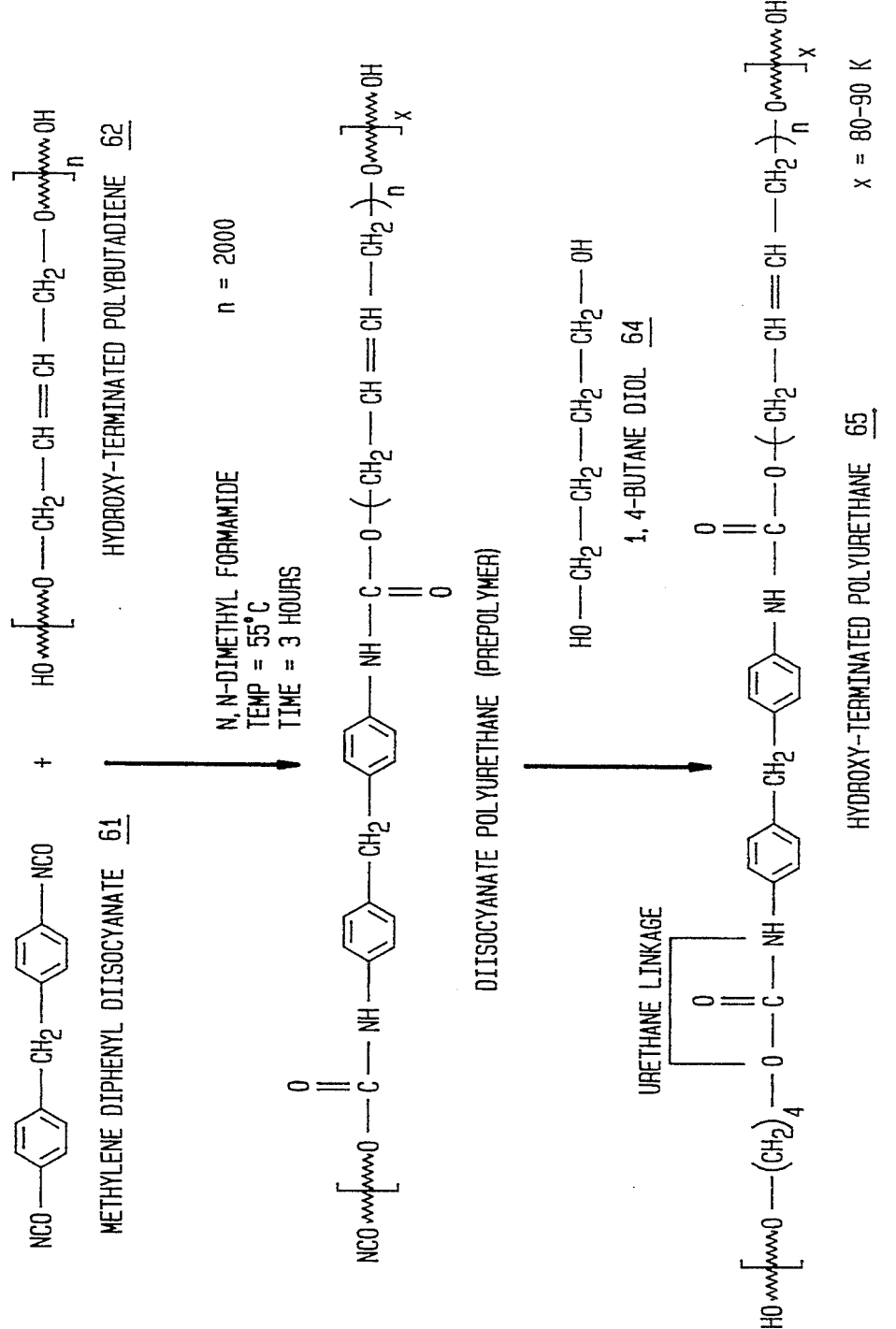

FIG. 9
REACTION SCHEME FOR THE HARD SEGMENT SURFACE MODIFICATION OF PU-2000
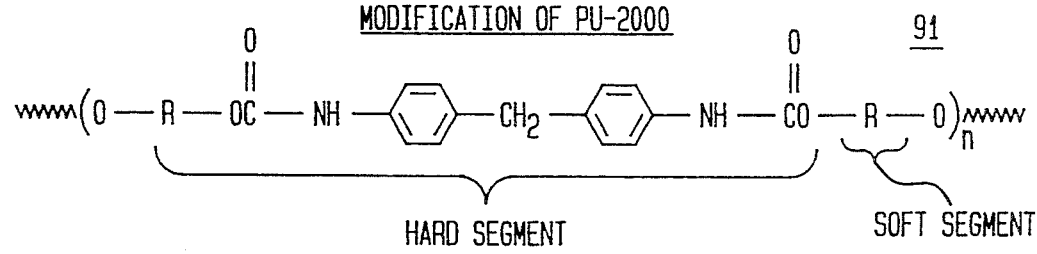
91
HARD SEGMENT | SOFT SEGMENT
CATALYST:
DIBUTYL TIN DILAURATE 92
STEP 1: REACTION WITH MDI
SOLVENT: $CCl_4$ (ANHYDROUS)
TEMPERATURE: 50-53°C
STEP 2: REACTION WITH EHDP
SOLVENT: DMSO (ANHYDROUS)
TEMPERATURE: 37°C
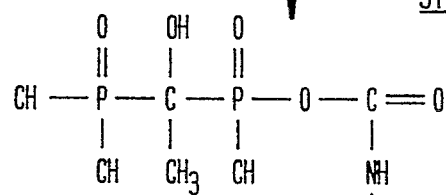
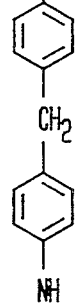
93
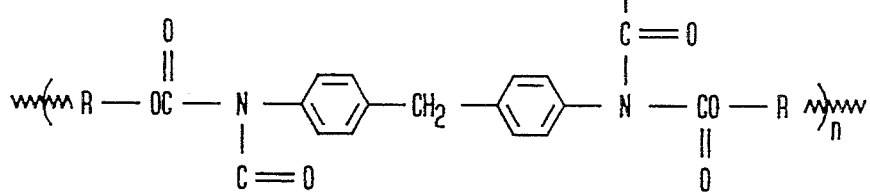
EHDP-CONTAINING
SURFACE-MODIFIED PU-2000
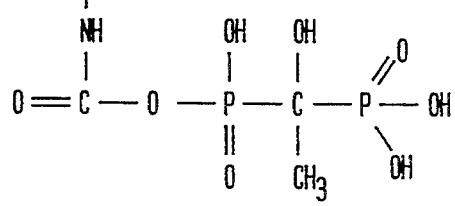

CALCIFICATION-RESISTANT SYNTHETIC BIOMATERIALS

GOVERNMENT RIGHTS

This invention was made with government support under Contract 5 R01 HL36574 awarded by the National Institutes of Health. The government has certain rights in the invention.

RELATIONSHIP TO OTHER APPLICATION(S)

This application is a continuation-in-part of PCT application PCT/US 93/05601 filed on Jul. 9, 1993 as a continuation-in-part of U.S. Ser. No. 07/910,941 filed on Jul. 9, 1992, now U.S. Pat. No. 5,296,583 the disclosure(s) of which are incorporated herein by reference.

BACKGROUND OF THE INVENTION

1. Field of the Invention

This invention relates generally to materials which are resistant to in vivo calcification, and more particularly, to calcification-resistant biomaterials, suitable for implantation in a living being, comprising a synthetic biocompatible polymer to which an anticalcification agent(s) is bound by stable, irreversible covalent bonds.

2. Description of the Related Art

This invention relates generally to materials which are resistant to in vivo calcification, and more particularly, to calcification-resistant biomaterials, suitable for implantation in a living being, comprising a synthetic biocompatible polymer to which an anticalcification agent(s) is bound by stable, irreversible covalent bonds.

More than 100,000 cardiac valve prostheses are placed in patients each year. Frequently, valve replacement surgery is the only means of treating cardiac valve disease. Currently used replacement valves include mechanical valves which may be composed entirely of a synthetic polymeric material such as polyurethane; bioprosthetic valves derived from bovine pericardium or porcine aortic valves; and aortic homografts.

Use of mechanical valves is frequently complicated by thrombosis and tissue overgrowth leading to valvular failure. Calcification is the most frequent cause of the clinical failure of bioprosthetic heart valves fabricated from porcine aortic valves or bovine pericardium. Human aortic homograft implants have also been observed to undergo pathologic calcification involving both the valvular tissue as well as the adjacent aortic wall albeit at a slower rate than the bioprosthetic heart valves. Pathologic calcification leading to valvular failure, in such forms as stenosis and/or regurgitation, necessitates re-implantation. Therefore, the use of bioprosthetic heart valves and homografts has been limited because such tissue is subject to calcification. Pathologic calcification also further complicates the use of synthetic vascular grafts and other artificial heart devices, such as ventricular assist systems, because its affects the flexibility of the synthetic polymers used to produce the devices.

The mechanism for pathological calcification of cardiovascular tissue is not understood. Generally, the term "pathologic calcification" refers to the deposition of calcium phosphate mineral salts in association with a disease process. Calcification may be due to host factors, implant factors, and extraneous factors, such as mechanical stress. There is some evidence to suggest that deposits of calcium are related to devitalized cells, and in particular, cell membranes, where the calcium pump ($Ca^{+2}$-$Mg^{+2}$-ATPase) responsible for maintaining low intracellular calcium levels is no longer functioning or is malfunctioning. Calcification has been observed to begin with an accumulation of calcium and phosphorous, present as hydroxyapatite, which develops into nodules which can eventually lead to valvular failure.

Research on the inhibition of calcification of bioprosthetic tissue has focussed on tissue pretreatment with either detergents or diphosphonates. Both of the aforementioned compounds tend to wash out of the bioprosthetic tissue with time due to blood-material interactions. Thus, these treatments merely delay the onset of the inevitable calcification process. To date, long-term prevention of calcification has been an unattainable result. Accordingly, there is a need for a means of providing long-term calcification resistance for bioprosthetic or synthetic heart valves and other implantable, or in-dwelling, devices which are subject to in vivo pathologic calcification.

Systemic use of anticalcification agents, such as diphosphonates, results in significant side effects on bone, and overall, growth. Site specific therapy offers treatment with low regional drug levels and minimal side effects.

There is a further need in the art for improved biomaterials which are calcification-resistant and thromboresistant. Attempts have been made to bond the anticoagulant heparin to the surface of biomaterials. However, the known heparin binding schemes result in products which exhibit only temporary surface anticoagulation effects. There is, thus, a need for biomaterials which offer long-term thromboresistance.

It is, therefore, an object of this invention to provide biomaterials for implantation in a mammal which have increased resistance to in vivo pathologic calcification.

It is another object of this invention to provide biomaterials for implantation in a mammal which have a long-term, or prolonged, resistance to in vivo pathologic calcification.

It is also an object of this invention to provide biomaterials for implantation in a mammal which have localized calcification inhibition and, hence, avoid the toxic side effects associated with systemic administration of anticalcification agents.

It is additionally an object of this invention to provide a method of fabricating and/or treating biomaterials for implantation in a mammal to render the biomaterials resistant to in vivo pathologic calcification.

It is yet a further object of this invention to provide a novel method of covalently bonding anticalcification agents, specifically polyphosphonates or other anticalcification agents bearing functionalities capable of epoxide derivatization, to biomaterials.

It is also another object of this invention to provide a novel method of irreversibly binding polyphosphonates to synthetic biomaterials for permanent calcification inhibition.

It is still a further object of this invention to provide a novel method of irreversibly binding heparin to the synthetic biomaterials for permanent thromboresistance.

SUMMARY OF THE INVENTION

The foregoing and other objects are achieved by this invention which provides, in one aspect thereof, a biomaterial for implantation in the interior of the body of a living being. The biomaterial has irreversibly bound thereto an effective amount of an anticalcification agent for rendering said biomaterial resistant to in vivo pathologic calcification.

The anticalcification agent(s) is bound to the synthetic biomaterial by a novel epoxide-based derivatization scheme, herein referred to as "epoxy-bridge incorporation," which results in stable, irreversible covalent bonding of the anticalcification agent to the synthetic biomaterial through epoxide linkages. FIG. 1 shows an illustrative reaction scheme and the resulting product, which, in this embodiment, is a phosphonated polyurethane wherein the polyphosphonate anticalcification agent is linked to the soft segment of a polyurethane via the phosphonate hydroxy groups. FIG. 5 shows an alternative reaction scheme, and resulting product, in which the polyphosphonate anticalcification agent is linked to the soft segment of a polyurethane by a less reactive alcoholic hydroxy functional group of the polyphosphonate anticalcification agent.

The term "biomaterial" as used herein denotes any synthetic biocompatible polymeric material which is known, or becomes known, as being suitable for indwelling uses in the body of a living being, i.e., which is biologically inert and physiologically acceptable, non-toxic, and insoluble in the environment of use.

Illustrative biomaterials suitable for use in the practice of the invention include naturally-derived polymers, such as cellulose or collagen-based materials, or synthetic polymers, whether hydrophilic or hydrophobic, including without limitation, polyurethane, polydimethylsiloxane, ethylene vinyl acetate, polymethyl methacrylate, polyamide, polycarbonate, polyester, polyethylene, polypropylene, polystyrene, polyvinyl chloride, polytetrafluoroethylene, polysulfone, or cellulose acetate. It is to be understood that the term polymer is to be construed to include copolymers, such as the copolymer of polyurethane and silicone.

In preferred embodiments, the anticalcification agent is an amino diphosphonate or other polyphosphonate.

Exemplary diphosphonates include 3-amino-1-hydroxypropane-1,1-diphosphonic acid (AHDP) and ethanehydroxydiphosphonate (EHDP), also known as 2-hydroxyethane bisphosphonic acid. In certain embodiments, other polyphosphonates, such as diethylentriaminepenta(methylenephosphonic acid) and aminotri(methylenephosphonic acid) are preferred. As used herein the term "polyphosphonate" includes compounds having two or more phosphonates per molecule. Such polyphosphonates are commercially available or can be synthesized by those of skill in the art. Additional illustrative examples include, without limitation, hexamethylenediaminetetra(methylenephosphonic acid) and diethylenetriaminopenta(methylenephosphonic acid). Of course, other amino-containing anticalcification agents, such as amino derivatives of phosphocitrate, would be suitable for incorporation into the practice of the invention.

The polyphosphonates may, thus, have any alkyl, aralkyl or aryl backbone structure and reactive hydroxy groups on the phosphonate moieties and less reactive hydroxy groups on the alkyl, aralkyl or aryl. In certain embodiments of the invention, the epoxide linkage is through the reactive hydroxy groups on the phosphonate moieties. In other embodiments, the epoxide linkage is through the hydroxy group on the alkane.

In an alternative embodiment, the calcification-resistant biomaterials of the present invention can be rendered resistant to in vivo thrombus formation by having an effective amount of the anticoagulant heparin irreversibly bound thereto by the epoxy-bridge incorporation techniques described herein.

In a method aspect of this embodiment of the invention, a thromboresistant polymeric material may be fabricated by:

forming a solution of heparin and a reactive polyfunctional epoxide to form a heparinepoxide monoadduct;

adding a solution of a prepolymerized biocompatible polymer to the monoadduct to form a mixture; and polymerizing the mixture.

Since the anticalcification agents are irreversibly bound to the biomaterial substrate by epoxide linkages, any anticalcification agent which has reactive hydrogen functionalities, such as amine, amide, alcohol, or carboxylic acid functionalities, for example, can be linked to a biocompatible elastomer via epoxy-bridge incorporation as described herein. Examples of other anticalcification agents include, without limitation, sulfaminotricarballyate, alpha amino oleic acid, pyrophosphate, statherin, polylysine, and polyarginine.

In a method aspect of the invention, synthetic calcification-resistant biocompatible polymeric materials are made by incorporation of polyphosphonate during primary polymerization of a biocompatible polymer or copolymer. In a specific illustrative embodiment, a calcification-resistant synthetic polyurethane is fabricated by the steps of:

forming a monoadduct of a polyphosphonate anticalcification agent and a reactive polyfunctional epoxide;

adding the monoadduct to a prepolymer base, illustratively a macroglycol, including active hydrogen functional groups, such as a polyol, polyester, or polyether;

adding diisocyanate as the second component of the polyurethane; and polymerizing the resultant mixture.

Illustrative polyfunctional epoxides which are suitable for use in the practice of the invention include diglycidyl butanediol ether, ethanediol diglycidyl ether, butanediol diglycidyl ether, and polyglycerol polyglycidyl ethers.

In still further method embodiments of the invention, synthetic calcification-resistant biocompatible polymeric materials are made by incorporation of polyphosphonate into prepolymerized biocompatible polymeric materials. In one specific illustrative embodiment, a solution of a polyphosphonate anticalcification agent and a reactive polyfunctional epoxide is formed in a solvent; a pre-polymerized biocompatible polymer which is soluble in the same solvent is added to the polyphosphonate/polyfunctional epoxide solution to form a mixture; and the mixture is polymerized. Of course, the pre-polymerized polymer could be dissolved in the same, or a compatible, solvent prior to contact with the polyphosphonate/polyfunctional epoxide solution.

In yet another method aspect of the invention, a calcification-resistant polymeric material is made by a technique which does not involve epoxy-bridge formation. In this embodiment, a diisocyanate-terminated prepolymer is formed from the soft segment and hard segment components of a polyurethane, and a chain extender to the diisocyanate-terminated prepolymer. In embodiments where the chain extender is a short chain diol, such as 1,4-butanediol, the product is an hydroxy-terminated polyurethane. The hydroxy-terminated polyurethane can be reacted with a polyphosphonate anticalcification agent via an epoxy-bridge incorporation technique of the type described herein to produce a polyphosphonate-terminated polyurethane.

In other embodiments, the chain extender is a polyphosphonate, which forms directly a phosphonate-terminated polyurethane.

In a still further method aspect of the invention, a calcification-resistant biomaterial may be made by:

forming a tetraester derivative of a polyphosphonate anticalcification agent;

reacting the tetraester derivative of a polyphosphonate anticalcification agent and a reactive polyfunctional epoxide to form a phosphonated epoxide monoadduct;

reacting the phosphonated epoxide monoadduct with an hydroxy-terminated polymer to form a tetraester-terminated biocompatible polymer. The tetraester-terminated biocompatible polymer can be hydrolyzed to a phosphonate-terminated biocompatible polymer with a mild hydrolyzing agent, such as bromotrimethyl silane, or by exposure to water. The result is a phosphonate-terminated polyurethane which is linked to the polymer via epoxide linkages with the hydroxy groups on the alkyl, aralkyl, or aryl backbone of the polyphosphonate anticalcification agent.

BRIEF DESCRIPTION OF THE DRAWING

Comprehension of the invention is facilitated by reading the following detailed description, in conjunction with the annexed drawing, in which:

FIG. 6 is an illustrative reaction scheme for the formation of an hydroxy-terminated polyurethane as the first step in a synthesis of diphosphonate-derivatized epoxidized polyurethanes;

FIG. 9 is an illustrative reaction scheme for coupling a hard segment modifier or spacer group, such as a bifunctional or polyfunctional isocyanate, to polyurethane followed by binding the anticalcification agent to the polymer through the isocyanate functional groups.

DETAILED DESCRIPTION

Figure 1:
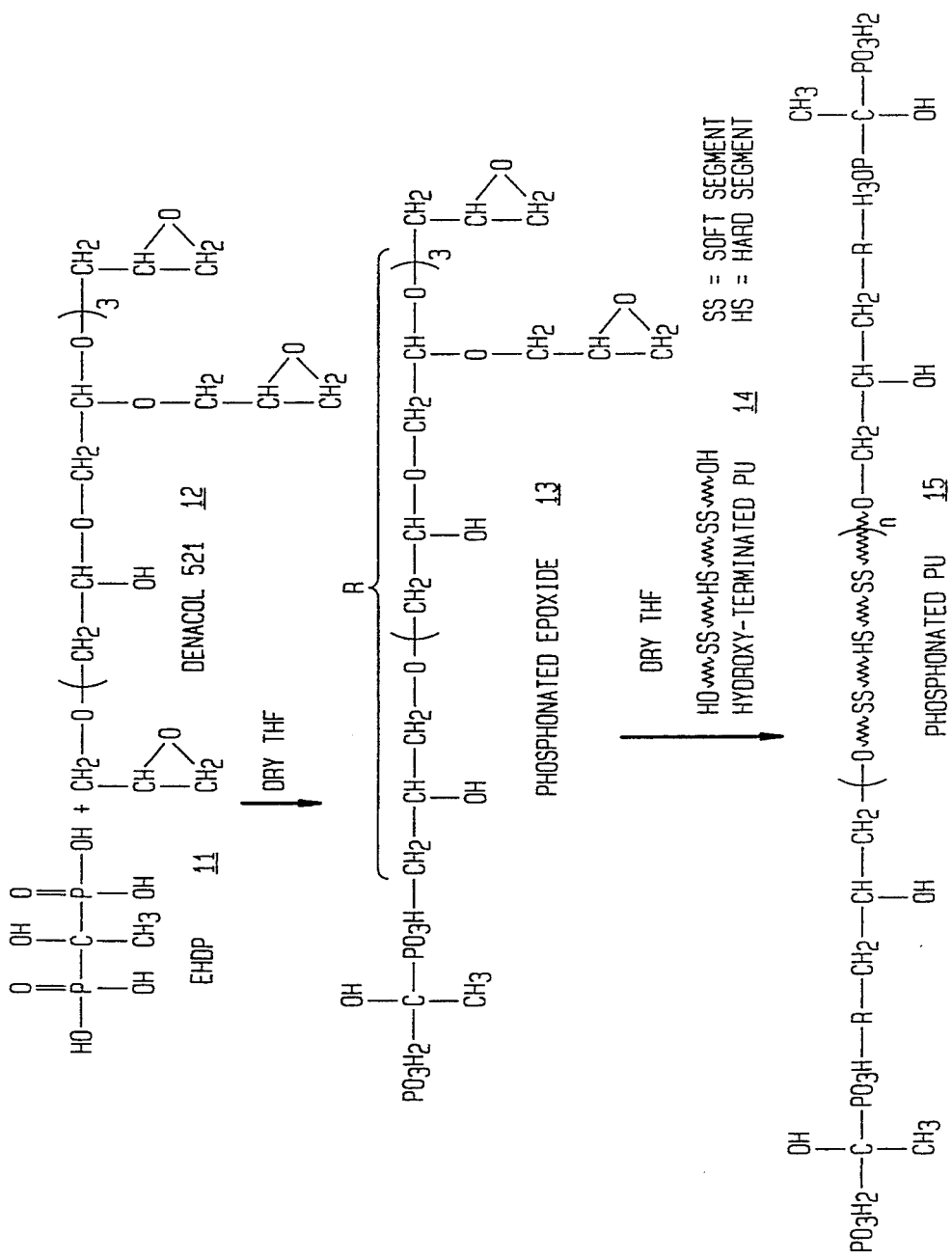
FIG. 1 is an illustrative reaction scheme for linking an anticalcification agent to synthetic biomaterials in accordance with the principles of the invention herein.

Given below are several specific illustrative techniques for producing calcification-resistant synthetic biomaterials in accordance with the principles of the invention.

Although the examples given are primarily directed to the preparation of calcification-resistant heart valve components, the techniques described herein are applicable to the creation of any other device, prosthesis, or implant comprising biomaterials of the type used for in-dwelling or surgically implanted devices. Such additional examples include, other cardiovascular devices, such as artificial hearts and ventricular assist systems, urinary catheters, and orthopedic devices which are also subject to pathologic calcification. In its broadest sense, the calcification-resistant materials can be configured to encompass, inter alia, knit or woven fabrics, single or plural filaments, extruded, cast or molded items, coatings on polymeric substrates or biological tissues, etc.

In accordance with the principles of the invention, polyphosphonate anticalcification agents have been successfully bound to synthetic biocompatible polymeric materials, such as medical grade polyurethane, by epoxy derivatization techniques. These techniques, using reactive bifunctional or polyfunctional epoxides, result in stable, irreversible covalent bonding of the diphosphonates to the biomaterial substrate (see, for example, Table I and FIGS. 2 and 3). The following procedures have resulted in the incorporation of 100 to 500 nM/mg polyphosphonate anticalcification agent into the polymeric material (see Table II).

It should be noted that the concentration range for the bound diphosphonate salt is given for purposes of illustration only, and can be varied by those of skill in the art because it is greatly in excess of the therapeutically effective amount. The ability to irreversibly bind a high concentration of anticalcification agent to the biomaterial (see FIG. 3), thereby directly placing a high concentration of pharmaceutic at the potential site of calcification over an extended period of time, is a significant advantage of this invention over the prior art.

Illustrative reactive bifunctional or polyfunctional epoxides suitable for use in the practice of the invention include, without limitation, diglycidyl butanediol ether (GAB), ethanediol diglycidyl ether, erythritol anhydride (EDE), butanediol diglycidyl ether (BDE), or the polyfunctional epoxides sold under the trademark Denacol by Nagasi Chemicals, Osaka, Japan. The Denacol epoxides are polyfunctional polyglycerol polyglycidyl ethers. For example, Denacol 512 has 4 epoxides per molecule and Denacol 521 (see FIG. 1, compound 12) has 5 epoxides per molecule.

Commercially available medical grade elastomers suitable for the practice of the invention include, in preferred embodiments, polyurethanes, or block copolymers which contain high molecular weight macroglycols linked together by a urethane group. Generally, polyurethane elastomers are produced by the rearrangement polymerization of diisocyanate and macroglycols. The main constituents are a hard segment which may be a diisocyanate, such as methylene diphenyl diisocyanate; a soft segment which may be a long chain, hydroxyl-terminated macroglycol as either a polyester or a polyether, illustratively polytetramethylene oxide; and a chain extender, such as a short chain glycol (e.g., 1,4-butanediol) or diamine.

Illustrative examples include, without limitation, Thiomer or Tecoflex 80A or 60A (trademarks of Thermedics Corp., Woburn, Mass.); polyurethane PU-2000 sold by CarboMedics Corporation, Austin, Tex.; Biomer (an aromatic co(polyetherurea) available from Ethicon, Somerville, N.J.); Cardiothane (a silicone-urethane copolymer available from Kontron, Inc., Everett, Mass.); or Pellathane, a polyurethane sold by Dow Chemical, Midland, Mich.

In specific advantageous embodiments of the invention, the anticalcification agent is a diphosphonate, such as ethanehydroxydiphosphonate (EHDP) or aminopropanehydroxydiphosphonate (APDP), or a polyphosphonate, such as aminotri(methylenephosphonic acid), and diethylentriaminepenta(methylenephosphonic acid). Other phosphonate anticalcification agents, however, are suitable for use in the practice of the invention. Moreover, any other anticalcification agent which is known, or becomes known, and has amine, amide, alcohol, or carboxylic acid functionalities, or any reactive hydrogen functionality, for example, can be linked to a biocompatible elastomer via the epoxide derivatization techniques described herein.

Other such anticalcification agents include sulfamino-tricarballylate (Analyt. Biochem., Vol. 132, p. 115, 1983); alpha-amino-oleic acid, Trans. Soc. Biomat., Vol. XIV. p. 60, 1991); pyrophosphoric acid, Science, Vol. 165, p. 1264, 1969); and the anticalcification protein, statherin and profamine sulfate (J. Biomed, Mater. Res., Vol. 25, p. 85, 1991); polylysine; and polyarginine.

In certain preferred embodiments, it is necessary to use the acid form since salts of polyphosphonates are not soluble in the organic solvents used in the reactions. Acid EHDP may be purified from a commercially available acid form or from the disodium salt. Acid EHDP (crude) is commercially available from Monsanto Chemical, St. Louis, Mo. under the trademark Dequest 2010. Disodium acid EHDP is commercially available from Norwich Pharmaceuticals, Norwich, N.Y.

Illustratively, the crude acid form or the disodium salt of EHDP is purified on a cation exchange resin, Dowex-50W (50x4-400; Dow Chemical Company, Midland, Mich.). The Dowex-50 resin is conditioned with alternating washes of 1M sodium hydroxide and 1M hydrochloric acid through seven cycles in a Buchner funnel. The final washing is done with hydrochloric acid. The resin is then washed with double distilled water until the pH of the effluent corresponds to the pH of the double distilled water. The resin is stored in water until use.

An appropriate ratio of a sodium or calcium salt of EHDP to ion exchange resin is 1 g of EHDP salt in 100 ml water to 32 g of resin. The resin mixture is stirred for four hours at room temperature. The Dowex-50 resin has a high capacity for sodium, and other cationic contaminants, and completely exchanges these contaminants with hydrogen to yield a pure solution of acid EHDP. The supernatant is then decanted from the resin and freeze dried under high vacuum. The purified acid EHDP may be recrystallized by any known technique, such as solvent evaporation with seed crystal addition.

I. EPOXY DERIVATIZATION TECHNIQUES

A. Incorporation of Polyphosphonate During Primary Polymerization

In general, a polyphosphonate or other epoxy-reactive anticalcification agent will be combined with a polyepoxide in a solution under reactive conditions, which will result in both adduct formation of the anticalcification agent with the epoxide, and retention of residual reactive epoxy groups for subsequent reactions with a polyol. The reactive anticalcification-epoxy-bridge compound will then be combined with a polyol or polyether prior to polyurethane polymerization via the usual diisocyanate addition. The unique feature of this general reaction scheme is the use of the polyepoxy compound as an epoxy-bridge forming agent, to incorporate anticalcification compounds within the framework of conventional polyurethane chemistry, or other biocompatible polymer chemistry in general.

Typically, a polyphosphonate anticalcification agent and a reactive polyepoxide are combined in a 1:1 molar ratio in a suitable solvent, such as THF DMAC, or DMF, for a time sufficient to form a monoadduct, illustratively 12 to 15 minutes. The monoadduct is combined with a prepolymer base in molar ratios ranging from 1:1 to 5:1 reactive adduct-epoxy groups per each potential hydroxy-terminus to form a resin having both the epoxide and the anticalcification agent. The prepolymer base may be, in the case of polyurethanes, a macroglycol such as a polyester or polyether. The second polymer component, which may be a diisocyanate for a polyurethane, is then added to the resin and polymerization is initiated.

Specific examples of prepolymer base components include, without limitation, polytetramethylene glycol, polethylene glycol, polypropylene glycol, or polyols containing heteroatoms such as sulfur or nitrogen with reactive bifunctional hydrogen functionalities. The polyols can range in molecular weight from a few hundred to a thousands. Exemplary diisocyanates include toluene diisocyanates, cyclohexyl diisocyanates, hexamethylene diisocyanates, naphthalene diisocyanate, 1-4-butane diisocyanate, etc.

In a specific illustrative embodiment, butanediol diglycidyl ether (25 $\mu$l) was added to a 0.1M solution of acid EHDP in 3 ml of dried tetrahydrofuran (THF) and stirred for 30 minutes, and preferably between 12 and 15 minutes. The resulting solution was combined with 3.45 g of polytetramethylene glycol (1000 mw) and stirred for an additional 30 minutes at room temperature. Polytetramethylene glycol is the prepolymer base for Tecoflex 80A. The second component of the copolymer, diisocyanate (0.93 g), was added to the solution and stirred until homogeneity was obtained. The polymerization reaction was catalyzed by the addition of 200 $\mu$l acetone-$FeCl_3$ (5 mg/ml). The mixture was then poured into a petri dish to polymerize in a vacuum oven at 100° C. (about 48 hours).

Figure 2:
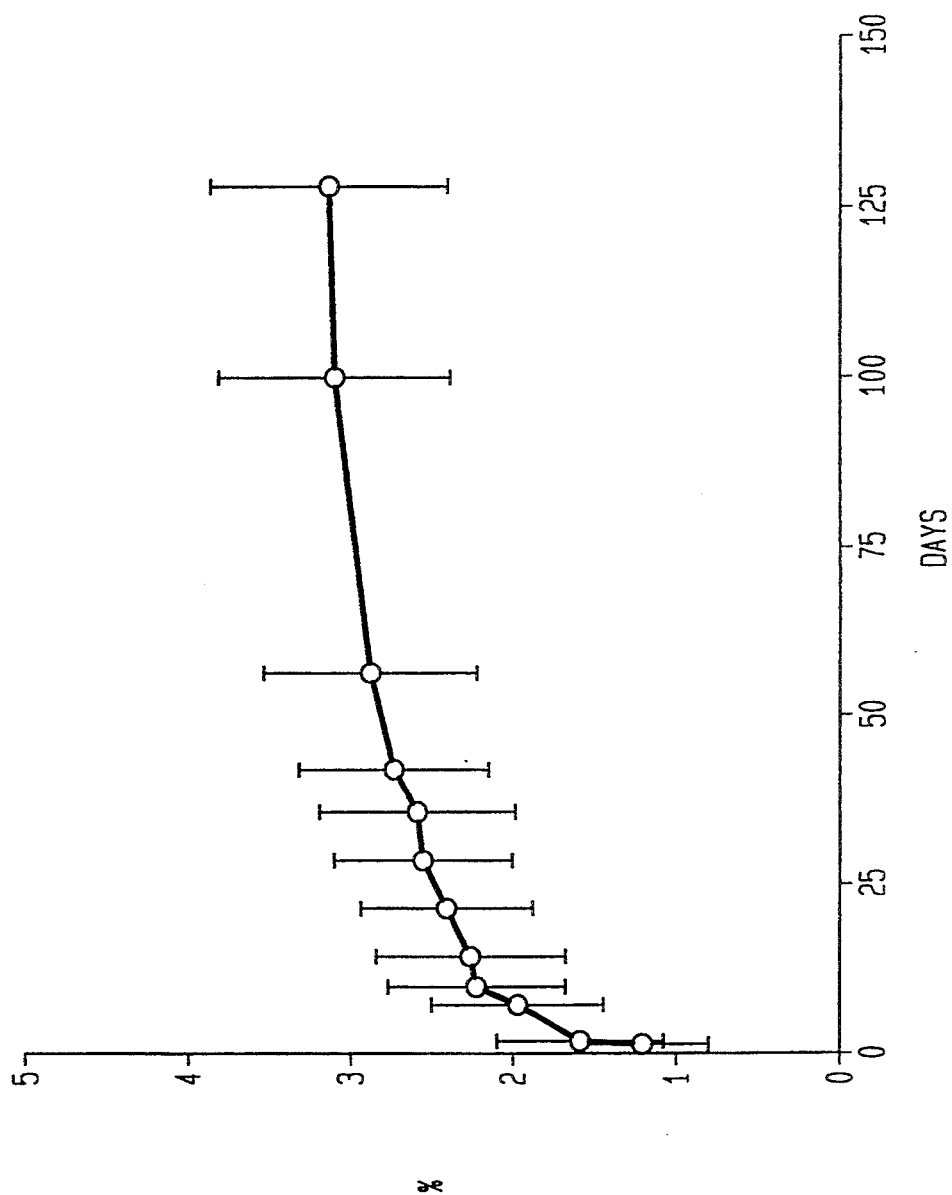
FIG. 2 is a graphical illustration showing dissociation of an anticalcification agent, EHDP, from a calcification-resistant polyurethane matrix fabricated in accordance with a method aspect of the invention.

Release studies were conducted by incorporating radioactive EHDP ($^{14}C$ EHDP) into Tecoflex 80A in accordance with the procedure described above. Referring to FIG. 2, the dissociation of epoxy-bridge linked EHDP from the resulting calcification-resistant polyurethane into a physiological buffer (pH 7.4) at 37° C. over a 128 day period is negligible. The data is expressed as the percentage released of the total bound. Thus, approximately 97% of the originally bound EHDP remains after at the 128th day.

The resulting calcification-resistant polyurethane can be dissolved in THF, dimethylacetamide (DMA), or dimethylformamide (DMF), and cast as films or used as coatings. In the alternative, the calcification-resistant polyurethane could be cast into molds.

B. Incorporation of Polyphosphonate Into Prepolymerized Materials

Polyphosphonates can also be irreversibly bound to prepolymerized materials via epoxy-bridge incorporation, illustratively, with hydroxy-terminated polyurethanes or amino-terminated polyurethane ureas, such as Mitrathane MPU5 (a polyetherurethane urea, a trademark of Polymedica, Denver, Colo.) or Biomer (a trademark of Ethicon, Somerville, N.J.).

In general, a polyphosphonate and a polyepoxide are combined in a 1:1 molar ratio in a suitable solvent, such as THF, for a time sufficient to form a monoadduct, illustratively 30 minutes. A prepolymerized polymer, which in some embodiments may be dissolved in a compatible solvent, is combined with the polyphosphonate/polyepoxide monoadduct in a ratio of one mole polymer to one mole epoxy group. The resulting mixture is dried and reacted in a vacuum oven for a period of time, illustratively 24 to 48 hours, at a temperature of about 50° to 75° C.

Referring to FIG. 1, an illustrative reaction scheme shows epoxy-bridge incorporation of a polyphosphonate into a polyurethane in accordance with a method aspect of the invention. A 0.1M solution of acidic EHDP (compound 11) in 2.0 ml THF was made. A reactive epoxide, Denacol 521 (a polyfunctional epoxide with five reactive groups per molecule sold by Nagasi Chemical, Osaka, Japan and shown as compound 12) was added to the EHDP solution in a concentration of 0.1M (148 mg) or 0.02M (29.6 mg). The mixture was stirred for 12 to 15 minutes at 37° C. to form the monoadduct, or phosphonated-epoxide compound 13. The biocompatible polymeric material, in this case an hydroxy-terminated polyurethane compound 14 (72,000 Mn, 1.52-1.60 MWD, 9.0512 g PU-2000 by CarboMedics, Inc., Austin, Tex.) was then added to the EHDP-Denacol mixture and stirred until homogeneous. In other embodiments, amino-terminated polymers, such as Mitrathane MPU5 (11.68 g) or Biomer (10.19 g) are used. Additional solvent (5-10 ml THF) was added to dilute the solution. The solution was then poured into a petri dish and placed in a 60° C. oven. Polymerization was permitted to take place under vacuum over about a 48 hour period. However, the vacuum was not applied until the air bubbles in the solution had disappeared. The result is phosphonated polyurethane compound 15.

Table I below shows the amount of EHDP incorporated (nM/mg) in the polyurethane biomaterial via epoxy-bridge incorporation and the percent released in vitro after 35 days in an isotonic HEPES buffer at pH 7.4 at 37° C. under perfect sink conditions. It should be noted that all EHDP which was not irreversibly covalently bound to the matrix material was released within 48 hours.

TABLE I

| Polyurethane | Epoxy | EHDP Incorporated (nM/mg) | % Released After 35 Days |
| --- | --- | --- | --- |
| Tecoflex | GAB | 71 | 3.9% |
| Tecoflex | BDE | 72 | 2.0% |
| Biomer | Denacol 521 | 81 | 2.2% |
| Mitrathane MPU5 | Denacol 521 | 68 | 35.5% |

*unbound drug was released within 48 hours

In still further illustrative embodiments of the invention, the diphosphonate EHDP and the polyphosphonates, aminomethyltriphosphonic acid and butylpentaphosphonic acid, were incorporated into pre-polymerized elastomers, specifically polyurethanes and silicone-polyurethane copolymers, in accordance with the procedure set forth above using Denacol 512 as the polyepoxide. Table II shows the amount of incorporated polyphosphonate in nM/mg.

TABLE II

| BASE POLYMER | TYPE OF POLY-PHOSPHONATE | AMOUNT OF POLY-PHOSPHONATE (nM/mg) |
| --- | --- | --- |
| PU-Si | ATMP | 100 |
| PU-Si | ATMP | 500 |
| PU-2000 | EHDP | 100 |
| PU-2000 | EHDP | 200 |
| PU-2000 | EHDP | 300 |
| PU-2000 | EHDP | 400 |
| PU-2000 | EHDP | 500 |
| PU-Si | EHDP | 100 |
| PU-Si | EHDP | 400 |
| PU-Si | EHDP | 500 |
| PU-2000 | DTMP | 100 |
| PU-2000 | ATMP | 100 |

Notes:
1) PU-2000: solvent cast polyurethane (Carbomedics, Inc., Austin, Tx)
2) PU-Si: polyurethane-silicone rubber copolymer (Dow Corning, Midland, MI)
3) EHDP: ethanehydroxydiphosphonate
4) ATMP: aminomethyltriphosphonic acid (Monsanto Chemical, St. Louis, MO)
5) DTMP: butylpentaphosphonic acid (Monsanto Chemical)

Figure 3:
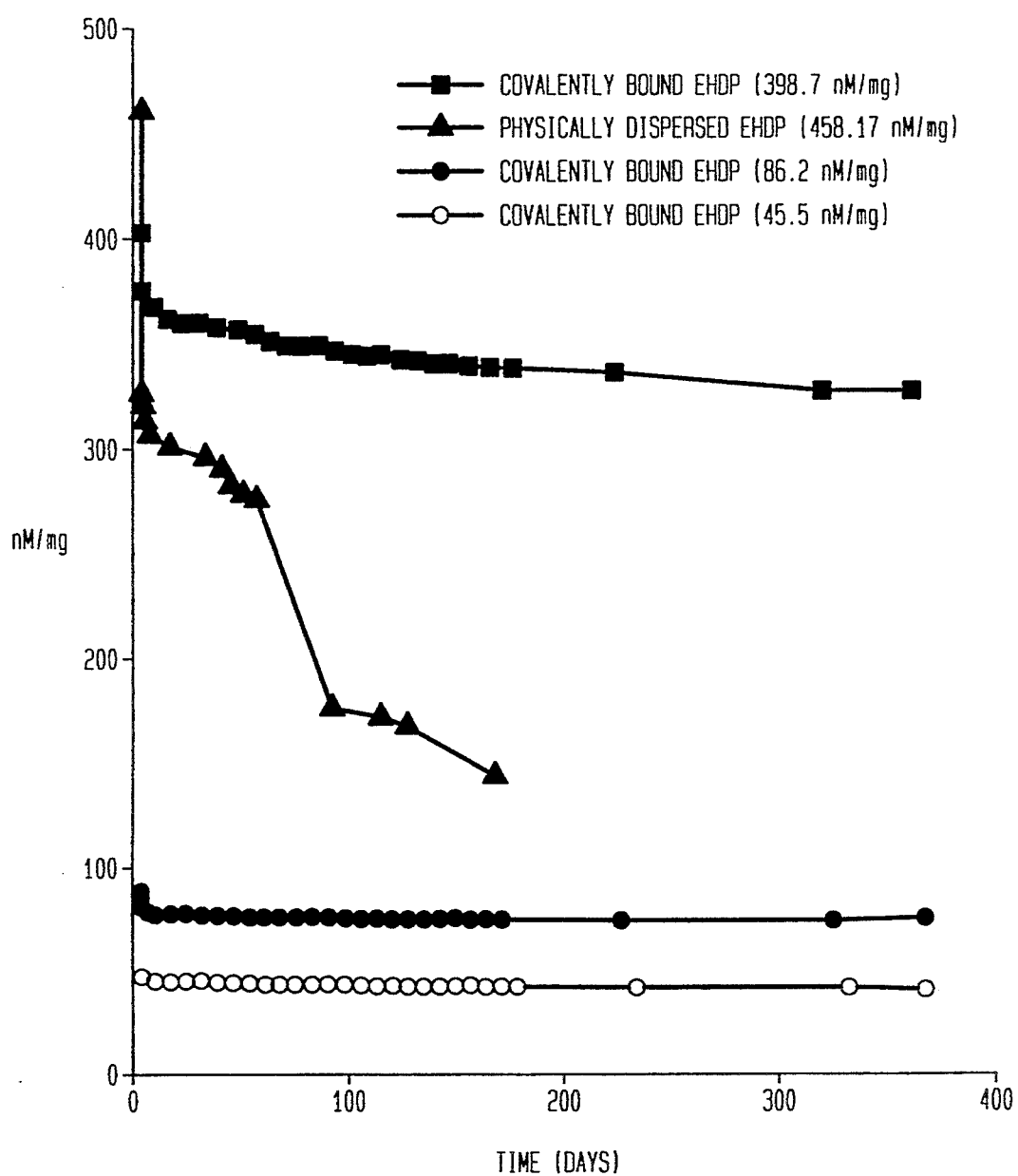
FIG. 3 is a graphical illustration showing the release profile of EHDP from hydroxy-terminated polyurethane matrices fabricated in accordance with a second method aspect of the invention as a function of drug loading.

In addition to the foregoing, an in vitro radioactive diphosphonate ($^{14}C$ EHDP) release study was conducted with several of the polyurethane-EHDP derivatives, formed by the epoxy-bridge incorporation technique, to evaluate release of EHDP from the polyurethane-EHDP matrix over time, and as a function of drug loading. FIG. 3 illustrates the release profile of EHDP from hydroxy-terminated polyurethane matrices as a function of drug loading (45.4 nM/mg to 398.7 nM/mg). As can be seen, there is virtually no significant dissociation of the covalently linked diphosphonate incorporated via this reactive scheme.

In the long-term binding stability studies (over 365 days) shown in FIG. 3, more than 75% of the total covalently bound EHDP was retained in the polymer matrix. The initial 25% unbound EHDP was released during the first two weeks. In contrast, a specimen of EHDP (458.17±1.3 nM) physically dispersed in a hydroxy-terminated polyurethane lost 26% of the EHDP in the first 24 hours, followed by release of 34% more in the next 60 days. The remaining 40% leached out slowly and continuously until exhausted.

The higher phosphonate content polyphosphonates are particularly advantageous for incorporation into biomaterials. Each molecule of a pentaphosphonate, for example, will have 2.5 times more phosphonate, on a molar basis, than EHDP. Thus, a greater amount of anticalcification agent can be irreversibly bound to the substrate material.

The calcification-resistant synthetic biomaterials of the present invention can be cast into molds; dissolved in solvents, such as DMA and THF, and cast into thin films or flexing leaflet membranes; combined with other compatible polymers; dip-coated on surfaces of other materials, including tissue-derived biomaterials to improve their biophysical stability.

The epoxy-bridge incorporation method can be adapted to irreversibly bind the anticoagulant heparin to a biocompatible polymeric material, such as polyurethane. The result is a thromboresistant biomaterial which is particularly suited for manufacturing devices for intravascular implantation. The heparin immobilized polymer can be mixed with the phosphonated polyurethanes described herein so as to produce a biomaterial which is both thromboresistant and calcification-resistant. Of course, the heparinized polyurethane can be used alone or homogeneously mixed with other polymers to render them thromboresistant. Other anticoagulants having structures similar to heparin, such as low molecular weight heparins or synthetic heparins may be immobilized by the epoxy-bridge incorporation technique.

Heparin (500 nM), such as that derived from porcine intestinal mucosa, is dissolved in a minimal volume of distilled water. About 0.2 ml dry THF is added. A polyfunctional epoxide, Denacol 512 (1:1 w/w ratio) is added to the heparin solution and the resulting mixture is permitted to react for a period of time, illustratively about 12 minutes, before it is added to a solution of a hydroxy-terminated polyurethane of known composition (4 mg, or 1:1 w/w ratio). The resulting mixture is reacted for about 24 hours, with constant stirring, and then cast into a film.

Release studies were conducted on heparinized polymer samples incorporating radiolabelled heparin. There was an initial burst phase release of heparin from the polymer matrix, possibly due to release of unreacted heparin from the matrix. However, after 4 days, the release stabilized, i.e., there was no further release, indicating that the remaining heparin was covalently bound to the polymer.

Heparinized polymer samples (1 mm×1 mm) containing 500 nM heparin were placed in dog plasma and incubated for 1 hour or 24 hours at 37° C. The plasma was then observed for clot formation time by the standard APPT Test. For comparative purposes, specimens of PU-2000, alkylated PU-2000, and an alkylated polyurethane-silicone copolymer were also incubated in plasma. The results are set forth in Table III below.

TABLE III

| Sample | Clotting Time (sec.) | | | | | Ave. Clot Time (sec.) |
|---|---|---|---|---|---|---|
| Incubated Plasma | 14.7 | 14.4 | 14.3 | 14.8 | — | 14.22 |
| PU-2000/1 hr | 15.8 | 14.8 | 15.8 | 14.3 | 15.9 | 15.32 |
| PU-2000/24 hrs | 33.3 | 33.6 | 33.5 | — | — | 33.46 |
| Hep. PU-2000 | NO CLOT EVEN AFTER 200 sec. | | | | | >200 |
| alk. PU-2000/1 hr | 14.7 | 13.8 | 14.4 | 13.9 | 13.9 | 14.14 |
| alk. PU-2000/24 hrs | 15.3 | 14.3 | 13.8 | 23.4 | 18.3 | 18.3 |
| alk. PU-Si/1 hr | 14.9 | 15.3 | 14.8 | 14.3 | 15.4 | 14.94 |
| alk. PU-Si/24 hr | 14.9 | 16.8 | 15.9 | 14.4 | 13.8 | 13.8 |

In all of the foregoing method aspects, the irreversible covalent binding of the polyphosphonate anticalcification agent was achieved through a reactive phosphonate hydroxy functional group as shown in FIG. 1. In still a further alternative embodiment of a method aspect of the invention, the polyphosphonate anticalcification agent is bound to the polymer at the less reactive alcoholic hydroxy functional group of the polyphosphonate anticalcification agent using a variation of the epoxy-bridge incorporation technique as shown in the illustrative preparatory scheme of FIG. 5. The result is a novel biocompatible polymeric material which can be hydrolyzed to a phosphonate-terminated polyurethane. In some embodiments, a deblocking agent, such as the mild hydrolyzing agent bromotrimethyl silane, is used to hydrolyze the ester groups. In other embodiments, exposure to an aqueous environment causes hydrolysis of the ester linkage.

Figure 5B:
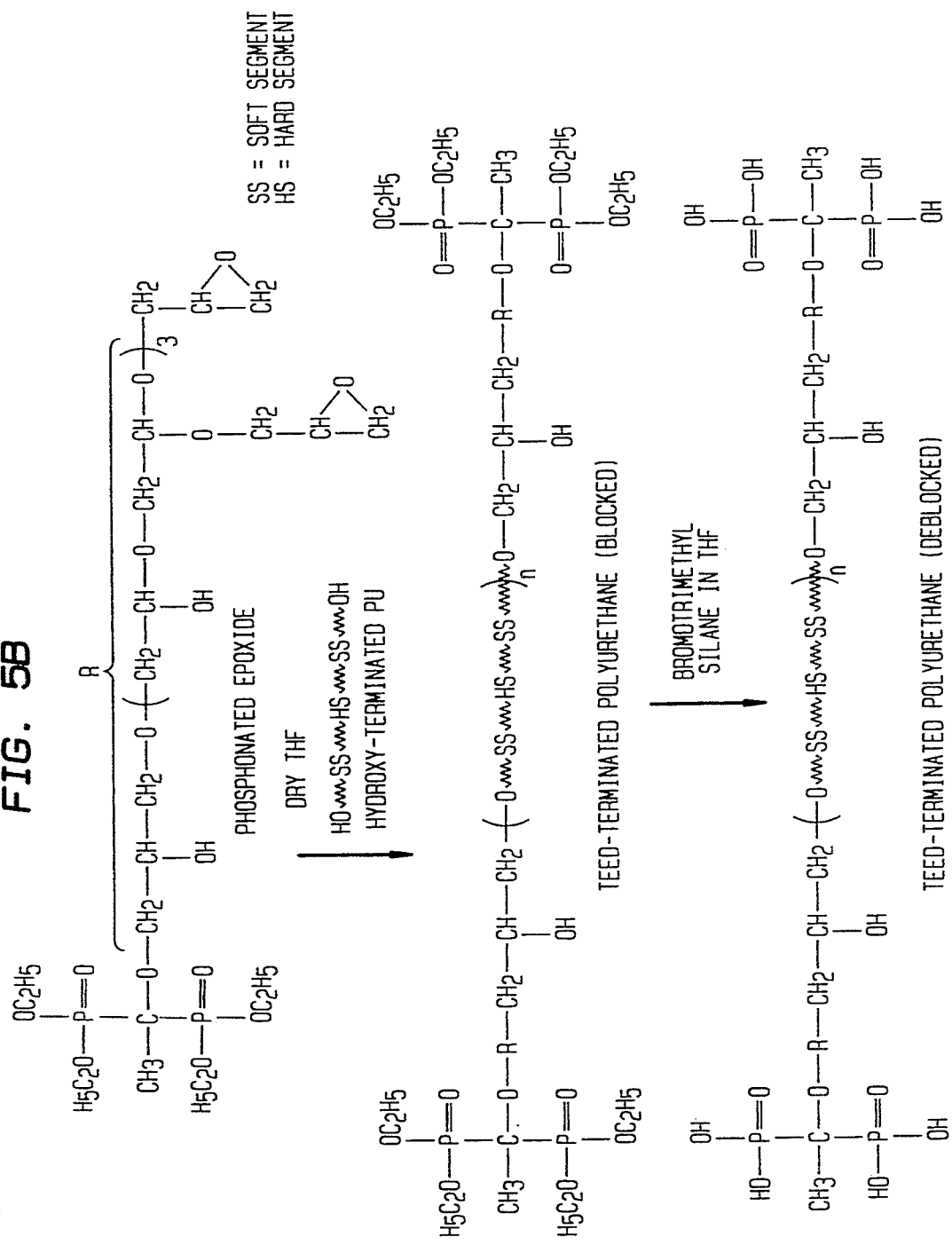
FIG. 5 is another illustrative reaction scheme for linking an anticalcification agent to synthetic biomaterials in accordance with the principles of the invention herein.

In a specific illustrative embodiment of the invention, a tetraester derivative of EHDP, specifically tetraethyl ethane-1-hydroxy-1,1-diphosphonate, is synthesized and then covalently bound to hydroxy-terminated polyurethane by an epoxy-bridge incorporation technique as shown in FIG. 5.

a. Synthesis of a tetraester derivative of a polyphosphonate anticalcification agent i.) A direct method generally requires the synthesis of dialkyl acetyl phosphonate from a trialkyl phosphite and acetyl chloride. The dialkyl acetyl phosphonate is then reacted with dialkyl hydrogen phosphite and dialkyl amine to yield tetraalkyl 1-hydroxyethylidene bisphosphonic acid (TEED). A specific illustrative embodiment is given below:

Triethyl phosphite (1.0 mole) was added dropwise with stirring to acetyl chloride (1.0 mole) over a period of about 2 hours. The reaction was maintained at a temperature of about 25° C. during this time. After all of the triethyl phosphite was added, the reaction mixture was stirred at room temperature for 2 more hours and then heated gently to evaporate the acetyl chloride. Distillation of the reaction mixture gave a 70% yield of the dialkyl acetyl phosphonate, specifically diethyl acetylphosphonate (b.p. 63°–65° C.).

Diethyl hydrogen phosphite (1.0 mole) and diethyl amine (1.0 mole) were combined in a round bottom flask. Diethyl acetylphosphonate (1.0 mole) was added dropwise, with stirring. The reaction mixture was maintained at a temperature of about 75° C. for an additional 2 hours after all of the diethyl acetyl phosphonate was added. The resulting mixture was distilled under reduced pressure to yield tetraethyl 1-hydroxyethylidene bisphosphonic acid as a pale yellowish liquid which crystallized at −15° C. into small needle-shaped crystals.

ii.) Tetraalkyl 1-hydroxyethylidene bisphosphonic acid can also be formed by the esterification of a polyphosphonate anticalcification agent, such as EHDP, with excess trialkyl orthoformate.

In a specific illustrative embodiment, EHDP (1.0 mole) and triethyl orthoformate (TEOF) (6 moles) were combined in a round bottom flask and heated to reflux for 1 hour, with rapid stirring. Excess triethyl orthoformate (100%) was added. Ethyl formate and ethanol, formed during reaction, were removed continuously by distillation. Heating was continued until only one phase remained and triethyl orthoformate began to distill. Removal of excess triethyl orthoformate yielded a yellowish liquid. Vacuum distillation of the yellowish liquid yielded pure tetraethyl 1-hydroxyethylidene bisphosphonic acid.

b. Binding of TEED to hydroxy-terminated polyurethane

In a specific illustrative embodiment, TEED and Denacol 521 were dissolved separately in dry THF and then mixed homogeneously for 30 minutes to form a phosphonated epoxide monoadduct. A prepolymerized hydroxy-terminated polyurethane, such as the polyetherurethane made hereinabove in the non-epoxy derivatization scheme, was dissolved in dry THF. The phosphonated epoxide monoadduct was added to the dissolved polyurethane and the mixture was allowed to react for 24 hours, with stirring.

A TEED-terminated polyurethane polymer was purified from the reaction mixture by precipitating and dissolving the polymer, three times in respective non-solvent (hexane, b.p. 60°–70° C.) and solvent (anhydrous THF) systems. This procedure removed unreacted TEED and low molecular weight phosphono-epoxide oligomers. The purified polymer was dried in a vacuum oven at 50° C. for 48 hours until constant weight was achieved.

The reactive phosphonate hydroxy functional groups of the TEED-terminated polyurethane are protected, or blocked, as esters. To obtain the phosphonate-terminated polyurethane, the ester functional groups were hydrolyzed, or deblocked, with bromotrimethyl silane to form hydroxy groups. A 25% solution of TEED-terminated polyurethane in dry dimethyl acetamide was placed in a three-necked flask. The three-necked flask was fitted with a Dean Stark apparatus via a reflux condenser. Bromotrimethyl silane (1:1 w/w) was added dropwise with continuous stirring. The reaction was heated to reflux and maintained at a temperature of 70° C. for 4 hours. Ethanol (b.p. 65° C.) was formed during the reaction and collected in the Dean Stark apparatus. When ethanol ceased to be released, refluxing was terminated and the deblocked, or phosphonate-terminated, polymer was precipitated in dry hexane.

The deblocked polymer was purified by alternate precipitation and dissolution, three times in respective non-solvent (hexane, b.p. 60°–70° C.) and solvent (anhydrous THF) systems. The deblocked polymer was then dried in a vacuum oven at 50° C. for 48 hours until constant weight was achieved.

C. Covalently Binding Polyphosphonate to Epoxidized Soft Segment

In yet another embodiment for forming calcification-resistant biomaterials, epoxy bridges are formed throughout the soft segment polyether chains in polyurethane molecules, rather than at terminal hydroxyl groups or alcoholic hydroxy groups as in the foregoing examples. This increases the potential capacity for covalently binding many types of compounds to the polyurethane. Epoxidized polyurethanes can be made calcification resistant by covalently binding anticalcification agents to the polyurethane. In addition, other desirable properties, such as resistance to thrombosis, can be achieved by binding an anticoagulant at the epoxidized sites.

Figure 7:
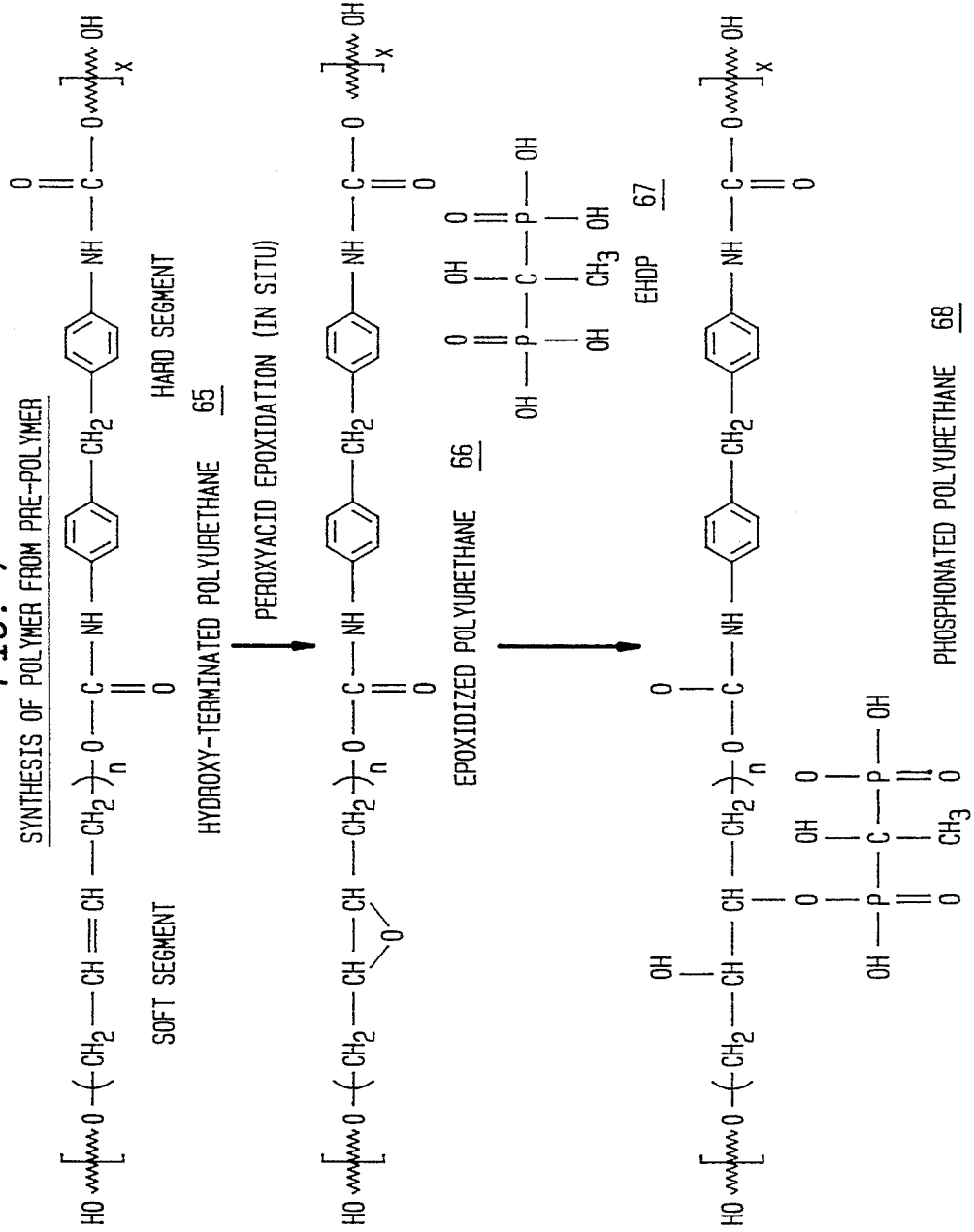
FIG. 7 is an illustrative reaction scheme for the epoxidation and covalent binding of EHDP to the soft segment of the hydroxy-terminated polyurethane prepared in accordance with FIG. 6 as the second step in the synthesis of diphosphonate-derivatized epoxidized polyurethanes.

Synthesis of diphosphonate-derivatized epoxidized polyurethanes involves two steps, as illustrated in FIGS. 6 and 7 which comprise an illustrative reaction scheme. First, a polyurethane base polymer is synthesized. An isocyanate-terminated prepolymer is prepared, and the base polymer is formed through reaction of the isocyanate-terminated prepolymer with a chain extender. Second, the polyurethane base polymer is modified. The unsaturated double bond in the soft segment of the polyurethane comprising the base polymer is epoxidized. Then, any desired compound which is reactive with an epoxide, such as the anticalcification agent diphosphonate, can be covalently bound to the epoxidized base polymer.

In a specific illustrative embodiment, various mole ratios of 4',4'-diphenylmethylene diisocyanate (MDI), hydroxy-terminated polybutadiene (HTPBTD; MW 2000), and 1,4-butane diol as a chain extender were used in a synthesis of a diphosphonate-derivatized epoxidized polyurethane.

A 250 ml reactor flask, containing 200 ml dry THF or DMF, was heated at 50° C. in a dry nitrogen atmosphere. After one hour, hot MDI (60° C.) was introduced into the vessel using a dry syringe attached to a cellulose acetate filter (Nalgene filter 0.45 mm) to remove insoluble precipitates.

Hot HTPBTD (60° C., water content less than 0.05%) was added dropwise to the reactor flask over a period of an hour with a syringe pump and constant stirring. During the course of addition, the temperature of the reaction mixture will rise due to the exothermic nature of the reaction. The temperature should not be permitted to rise above 80° C. A circulating water bath was used to control the temperature in these specific embodiments. After all of the HTPBTD was added, the solution was allowed to react for an additional 3 hours at 80° C. This results in the formation of an diisocyanate-terminated prepolymer (compound 63).

Next, the temperature of the diisocyanate-terminated prepolymer was reduced to 60° C. Dry 1,4-butane diol was added dropwise over a period of 30 minutes with constant stirring. The temperature of the reaction mixture should be maintained below 80° C. The reaction was permitted to continue for 2 hours and the solvent was evaporated to leave a viscous mass.

The viscous mass was spread evenly on a hot Teflon coated plate (80° C.). The mass was cured in a vacuum oven at 90° C. for 48 hours under a nitrogen atmosphere and then exposed to room temperature. After curing, the polymer was again dissolved in THF or DMAC and then precipitated in double distilled water so as to remove the impurities and unreacted chemicals from the polymer mass. The precipitated material was then dried in a vacuum oven at 50° C. for 48 hours. The result is the polyurethane base polymer (Compound 65).

FIG. 7 is directed to an illustrative reaction scheme for the epoxidation and covalent binding of EHDP to the soft segment of the polyurethane base polymer. The epoxidation was done, in some embodiments, in accordance with a modification of the procedure described in Vernekar, et al., *J. App. Poly. Sci.*, 44:2107–2114 (1992). Typically, formic acid (0.25 moles) and $H_2O_2$ (0.75 moles) was added dropwise to 20 g. of the base polymer dissolved in 120 ml DMAC or THF. The reaction mixture placed in a water bath at 55° C., and was allowed to reflux for 3 hours, with stirring. This procedure converts the unsaturated carbons within the soft segment into oxirane rings. After the reaction is complete, the modified polymer (Compound 66) was precipitated in hexane and dried at 50° C. for 48 hours in a vacuum oven. The epoxy equivalent number (i.e., the weight of an epoxy resin in grams which contains one equivalent of epoxide group) of the modified polyurethane was determined by titration using methods known in the art.

Based on the epoxy number of the epoxidized base polymer (Compound 66) established by titration, covalent binding of a diphosphonate, such as EHDP, was carded out. The epoxidized base polymer was dissolved in THF or DMAC. To this solution, EHDP dissolved in either THF or DMAC, was added and mixed until the solution was homogenous. The addition of EHDP to epoxidized base polymer was done, in this example, in the ratio of 4:1 (w/w). In order to activate the oxirane rings from the polymer chain, a catalyst (Imidazole; 0.01M) was added to the reaction mixture. The solution was then refluxed for three hours resulting in the binding of EHDP to one of the carbons and, at the same time, formation of a hydroxyl group on the adjacent carbon. Once the reaction was complete, the polymer was precipitated in n-hexane and purified by repeated dissolution and precipitation in respective solvent and nonsolvent systems. Finally, the polymer was dried in a vacuum oven at 50° C. for 48 hours to constant weight. The result is a phosphonated polyurethane (Compound 68).

Figure 8:
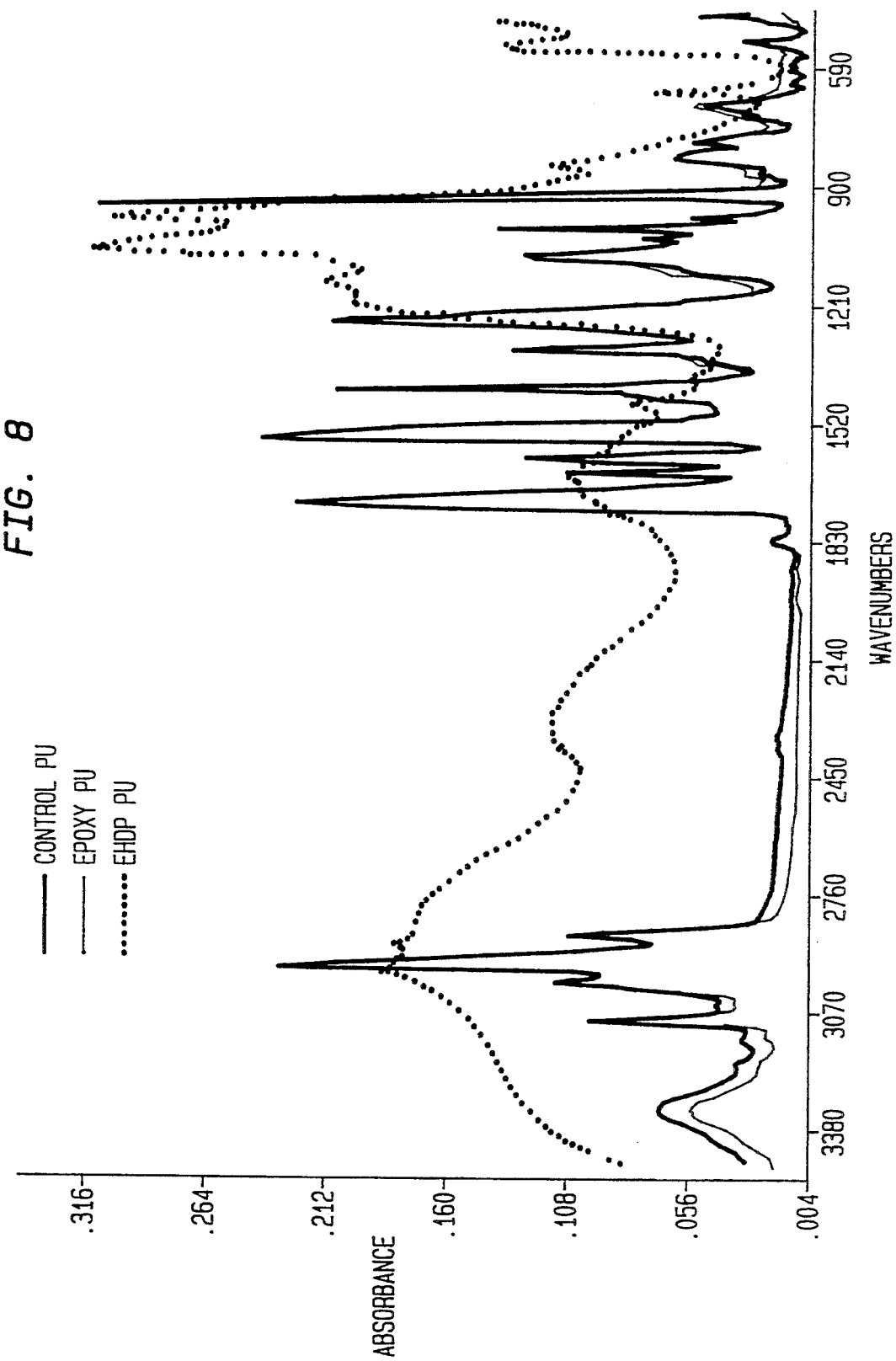
FIG. 8 is a graphical representation of the overlaid ATR-FTIR spectra of polyurethane (PU-2000), epoxidized polyurethane (FIG. 7, Compound 66), and the EHDP-epoxidized polyurethane (FIG. 7, Compound 68)

FIG. 8 shows the overlaid ATR-FTIR spectrum of the base polyurethane (PU-2000), epoxidized polyurethane (Compound 66), and the EHDP-epoxidized polyurethane (Compound 68). On comparing the base polymer with the epoxidized base polymer, it is evident that the unsaturated C=C bonds contributed by the soft segment of HTPBTD were converted to oxirane functional groups. Close observation in the finger print regions 650–1350 cm$^{-1}$ show major changes. However, covalent binding of EHDP through the oxirane ring, results in a major change in the IR spectra. A broad —OH peak contributed by the acidic phosphonate —OH groups and the alcoholic —OH formed due to the opening of the ring was clearly seen in the region around 3200–3400 cm$^{-1}$. Peaks between 1210 cm$^{-1}$ and 800 cm$^{-1}$ show the various bonding patterns which are characteristic of P—C, P—OH, and P=O.

II. Non-Epoxy Derivatization Techniques

In an alternative embodiment, polyphosphonates are covalently bound to a polyether or polyester polyurethane by a method which is not epoxide based. In general, a diisocyanate-terminated prepolymer is formed by reacting the hard and soft segment components of a polyetherurethane, e.g., a diisocyanate, such as 4',4'-diphenylmethylene diisocyanate (MDI), and a polyol, such as poly(tetramethylene glycol) (PTMG). Then, the chain extender is added to the diisocyanate-terminated prepolymer. In some embodiments, the chain extender is 1,4-butanediol which produces an hydroxy-terminated polyurethane. The hydroxy-terminated polyurethane may be further reacted with a polyphosphonate anticalcification agent to form a phosphonate-terminated polyurethane. In other embodiments, the chain extender is a polyphosphonate anticalcification agent, such as EHDP, which produces directly a phosphonate-terminated polyurethane.

In order to illustrate this method EHDP terminated polyether urethane is synthesized in solution using various molar ratios of 4',4'-diphenylmethylene diisocyanate (MDI), poly(tetramethylene glycol) (PTMG) with EHDP as the chain extender.

100 ml of dry DMF is placed in a 250 ml reactor flask and heated to 60° C. in a dry nitrogen atmosphere for one hour. Hot (60° C.) MDI is introduced into the reactor flask with a dry syringe fitted with a cellulose acetate filter (Nalgene filter 0.45 mm). Then, hot (60° C., water content less than 0.05%) PTMG is added dropwise to the MDI solution for a period of one hour, with constant stirring. The temperature of the resulting exothermic reaction should be controlled to 80° C. or less, and preferably in the range of 65°–70° C. Higher temperatures permit undesirable cross-linking during processing. A circulating water bath, for example, can be used to maintain the appropriate temperature. After addition of all of the PTMG, the solution is allowed to react for an additional 3 hours at 80° C. The result is the diisocyanate-terminated prepolymer.

The diisocyanate-terminated prepolymer solution is cooled to a temperature of about 60° C. prior to addition of EHDP. A 10% EHDP in dry DMF solution is added dropwise over a period of 30 minutes with constant stirring. This reaction is exothermic and the temperature is maintained at about 65°–70° C. The reaction is allowed to continue for 2 hours at about 65°–70° C. When the solvent is evaporated, a viscous semisolid material remains.

The viscous semisolid material is spread evenly onto a hot (80° C.) teflon coated plate. The material is then kept in a vacuum oven under nitrogen at 90° C. for 48 hours. Exposure to room temperature finalizes the curing of the viscous material into an EHDP-terminated polyurethane in accordance with the invention.

The times of reaction are merely illustrative and can be easily modified by a person of ordinary skill in the art. The reaction progress may be monitored for completeness by, for example, infrared spectroscopy or any other method to determine the diisocyanate content.

In yet another embodiment of this method aspect of the invention, the hard segment component and the soft segment component can be combined neat for a solvent-free reaction.

Of course, modifications of this method can be applied to bind polyphosphonates to polyurethane-silicone copolymers, ethylene vinyl acetate, and the like.

Experimental Section:

in vitro Studies

In addition to the release studies reported hereinabove, calcium diffusion studies and water absorption studies were conducted on specimens of EHDP-polyurethanes.

The presence of EHDP greatly reduces the immediate calcium influx across a polymer membrane as demonstrated in calcium diffusion studies wherein samples of derivatized and underivatized membranes (0.2±0.0038 mm thick) were mounted between two cells of a diffusion chamber. The donor cell contained a 45% solution of calcium chloride and the receptor cell contained 0.05M (pH 7.4) Tris buffer. The receptor cell liquid was analyzed for calcium content at various time periods. The cumulative amounts of calcium diffused across the underivatized membranes was found to be 5.93±3.2 μg. After 24 hours, these membranes attained equilibrium during which a steady diffusion of calcium was observed with the average diffusion of 3.742 μg/day. EHDP derivatized polyurethane samples permitted 50% or less Ca$^{+2}$ diffusion than control samples. The calcium transport decreased with increasing amounts of covalently bound EHDP. The rate of calcium diffusion for TEED-blocked polyurethane is less than for phosphonate-terminated polyurethane bound through the phosphonate functional group as in FIG. 1. The retardation of calcium ion transport implies that the EHDP bound to the polymer does indeed interact with ionized calcium.

Water absorption of samples of derivatized and underivatized polymers was determined by immersing the sample films (1×1 cm$^2$; 0.2±0.0038 mm thick) in deionized, double distilled water at 37° C. for 72 hours. The adsorbed water content of each specimen was evaluated by the weight difference before and after the immersion. The derivatized polymers were found to be more hydrophilic than then un-derivatized control samples. The results of this study demonstrated that hydrophilicity of the samples increased with increasing amounts of incorporated EHDP. Increased hydrophilicity can contribute to thromboresistance.

When analyzed by ESCA and FTIR-ATR studies, the bound EHDP was found to be incorporated in the soft segment of the polyurethane.

Synthetic Biomaterial in Rat Subdermal Model

The calcium content of calcification-resistant polyurethane specimens fabricated in accordance with the present invention was determined by atomic absorption spectroscopy following 60 days subdermal implantation in weanling male rats (3 weeks). The results are depicted on FIG. 4 which is a graphical illustration of the calcium content of several synthetic biomaterial specimens, in μg/mg, following subdermal implantation in a rat for 60 days.

Figure 4:
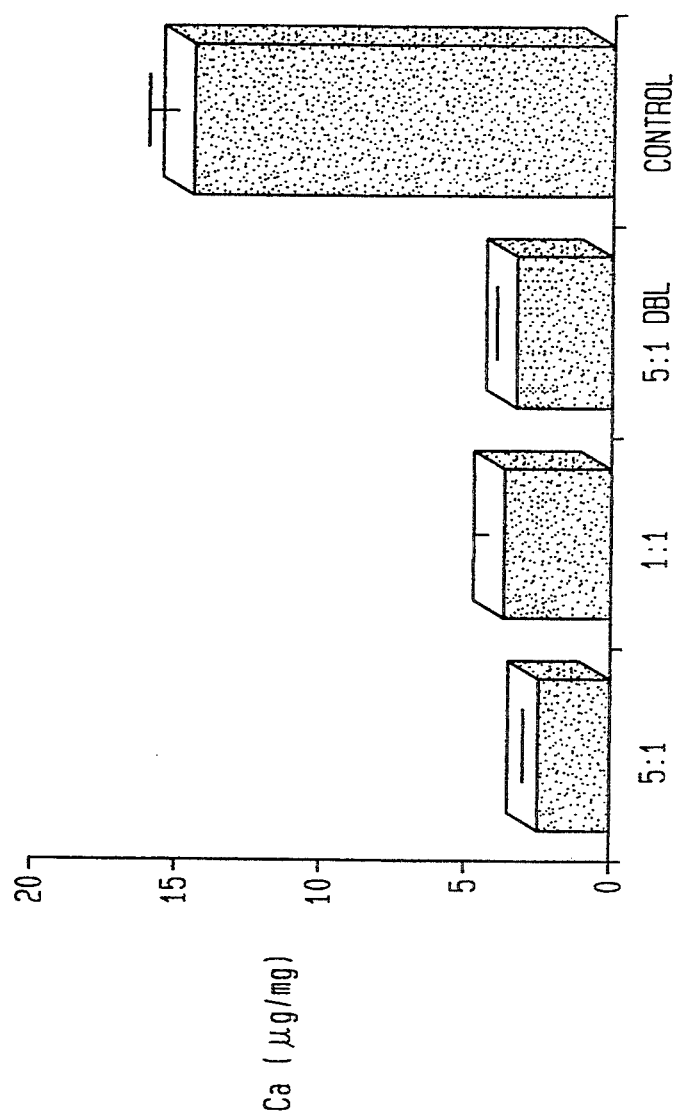
FIG. 4 is a graphical illustration of the calcium content ($\mu$g/mg) of several synthetic biomaterial specimens in accordance with the invention following subdermal implantation in rats for 60 days.

Synthetic biomaterial specimens were prepared in accordance with the method described above in Sec. B for the study shown in FIG. 3. The components of the synthetic biomaterial specimens were polyurethane (Mitrathane, MPU-5), EHDP, and Denacol 521. Referring to FIG. 4, the legend "5:1" refers to a polyurethane-based polymer wherein the concentrations of the reactive binding components are 0.1M Denacol 521 to 0.02M EHDP; "1:1" refers to equimolar concentrations of EHDP and Denacol 521 (0.02M); and "5:1 dbl" refers to 0.2M Denacol 521 to 0.04M EHDP. The "control" was Mitrathane.

A calcification-resistant synthetic biomaterial specimen and a control specimen were implanted in two subcutaneous pouches dissected in the ventral abdominal wall of weanling rats (male, CD, Sprague-Dawley, weighing 50–60 gm). After a period of 60 days, the specimens were removed and examined for calcification by measuring the level of $Ca^{+2}$ ions.

Referring to FIG. 4, diphosphonate-derivatized Mitrathane polyurethane did not calcify following subdermal implantation in a rat for 60 days, whereas the control Mitrathane polyurethane implants did. Clearly, FIG. 4 demonstrates a statistically significant reduction in calcium content for the novel synthetic biomaterial specimens of the present invention as compared to the control.

In an alternative embodiment, derivatization of polytetramethyleneglycol prior to polymerization led to the synthesis of another EHDP derivatized polyurethane with a hydroxy-terminated polytetramethyleneglycol soft segment (2000 molecular weight). The resulting polymer was used as a surface coating on various substrates, specifically Mitrathane and glutaraldehyde cross-linked pericardium. Inhibition of calcification was studied in a 60 day rat subdermal model as reported above. The results are reported in Table IV which gives the calcium content of the specimen, in μg/ng, following 60 days of implantation.

TABLE IV

| Sample | N | $Ca^{++}$ (μg/mg) |
| --- | --- | --- |
| Mitrathane (control) | 10 | 12.57 ± 0.86 |
| EHDP-Polyurethane (coated) | 10 | 0.25 ± 0.04 |
| GLT-crosslinked Pericardium | 10 | 226.9 ± 23.5 |
| Mitrathane (unimplanted) | 10 | 0.14 ± 0.004 |
| Pericardium (unimplanted) | 10 | 0.28 ± 0.004 |

As can be seen in Table IV, the "epoxy-bridge incorporation" technique is suitable for the synthesis of calcification-resistant materials which may be used as coatings. The EHDP-epoxy-polyurethane coated Mitrathane did not calcify as compared to controls. Thus, epoxy-bridge formation with polyphosphonate effectively inhibits calcification irrespective of whether the calcification-resistant material is incorporated throughout the polymer matrix, or via a surface coating as demonstrated by the data in Table IV.

In the foregoing illustrative embodiments, the soft segment, or polyether segment of a polyurethane, was modified. In a further embodiment of the invention, the hard segment, or diisocyanate segment, was derivatized to produce a calcification-resistant polyurethane. More specifically, in a specific illustrative embodiment, a diphenyl isocyanate derivative was covalently linked to the hard segment of a commercially available, medical grade polyurethane. The result was a side branch with a configuration comparable to the hard segment itself. Advantageously, the derivatized hard segment is reactive and can provide additional sites of binding for anticalcification agents, such as diphosphonates, or other active agents, such as the anticoagulant heparin. in vivo Experiments demonstrated that polyurethane with the derivatized hard segment, as well as polyurethane with the derivatized hard segment which has been covalently bound to a diphosphonate, resisted calcification in a rat subdermal model as compared to a non-modified polyurethane.

Referring to FIG. 9, a reaction scheme for binding a diphosphonate to the hard segment of a polyurethane via an allophanate linkage is shown. The synthetic scheme illustrated in FIG. 9 involves coupling a hard segment modifier or spacer group, such as a bifunctional or polyfunctional isocyanate, to polyurethane followed by binding the anticalcification agent to the polymer through the isocyanate functional groups.

In a specific illustrative embodiment, a medical grade polyurethane, specifically PU-2000 (available from CarboMedics, Austin, Tex.) was coupled with methylene diphenyl diisocyanate (MDI). A homogenous 20% solution of PU-2000 in dry THF was cast into a sheet on a Teflon coated metal plate. The cast film was cured in a vacuum oven at 50° C. for 48 hours to remove all traces of the solvent. The dried film was cut into 3×3 $cm^2$ specimens and transferred to a two-necked round bottom flask containing 225 ml of anhydrous $CCl_4$ and a magnetic stirring bar. Hot purified and filtered MDI was carefully added to the round bottom flask. The reaction solution was blanketed with dry $N_2$ gas. A catalyst, dibutyltin dilaurate (DBTDL; 0.1% v/v) was added to facilitate the formation of allophanate linkages with free isocyanate functional groups.

The addition of MDI to PU-2000 was done in the ratio of 2:1. Varying the reaction time alters the amount of MDI surface grafting. In preferred embodiments, the reaction time was between about 15 minutes to 60 minutes, After reaction, the $CCl_4$ solvent was decanted from the flask and the polyurethane specimens were retrieved and washed five times in anhydrous $CCl_4$ so as to remove any surface-adhered, unreacted MDI. The washed specimens were dried in a vacuum oven at 65° C.

Next, a diphosphonate, specifically EHDP, was coupled to the surface of the specimens by reaction with the free isocyanate functional groups. The specimens were placed in a solution containing 10% EHDP in anhydrous DMSO. The EHDP solution also contained 0.04 ml DBTDL. The specimens in the solution were shaken on an orbital shaker, for a period of time commensurate with reflux of the solvents, in a 37° C. oven. The specimens were then washed five times in anhydrous DMSO and dried in separate containers at 65° C. in a vacuum oven. The result was an EHDP-containing, surface-modified PU-2000 (Compound 93).

Solubility studies showed that surface-modified PU and EHDP-containing, surface-modified PU-2000 are insoluble in THF and DMAC. However, the flexibility and elastic properties remain substantially the same as unmodified PU-2000.

Immersion of the specimens in water revealed that the unmodified PU-2000 absorbs little water. However, the oo-data demonstrate that the 60 minute modified samples absorbed about 3.25 times more water than the other samples. This suggests that as the length of the reaction period increases, so does the degree of cross-linking. This also indicates that EHDP binding through allophanate linkages increases the polymer's hydrophillicity.

ESCA studies showed that the phosphorous concentration significantly increases as the time of the surface modification reaction was increased (49.2% increase over the 15 minute by the 30 minute specimens). The increase in phosphorous concentration indicates that the binding of EHDP was successful.

Figure 10:
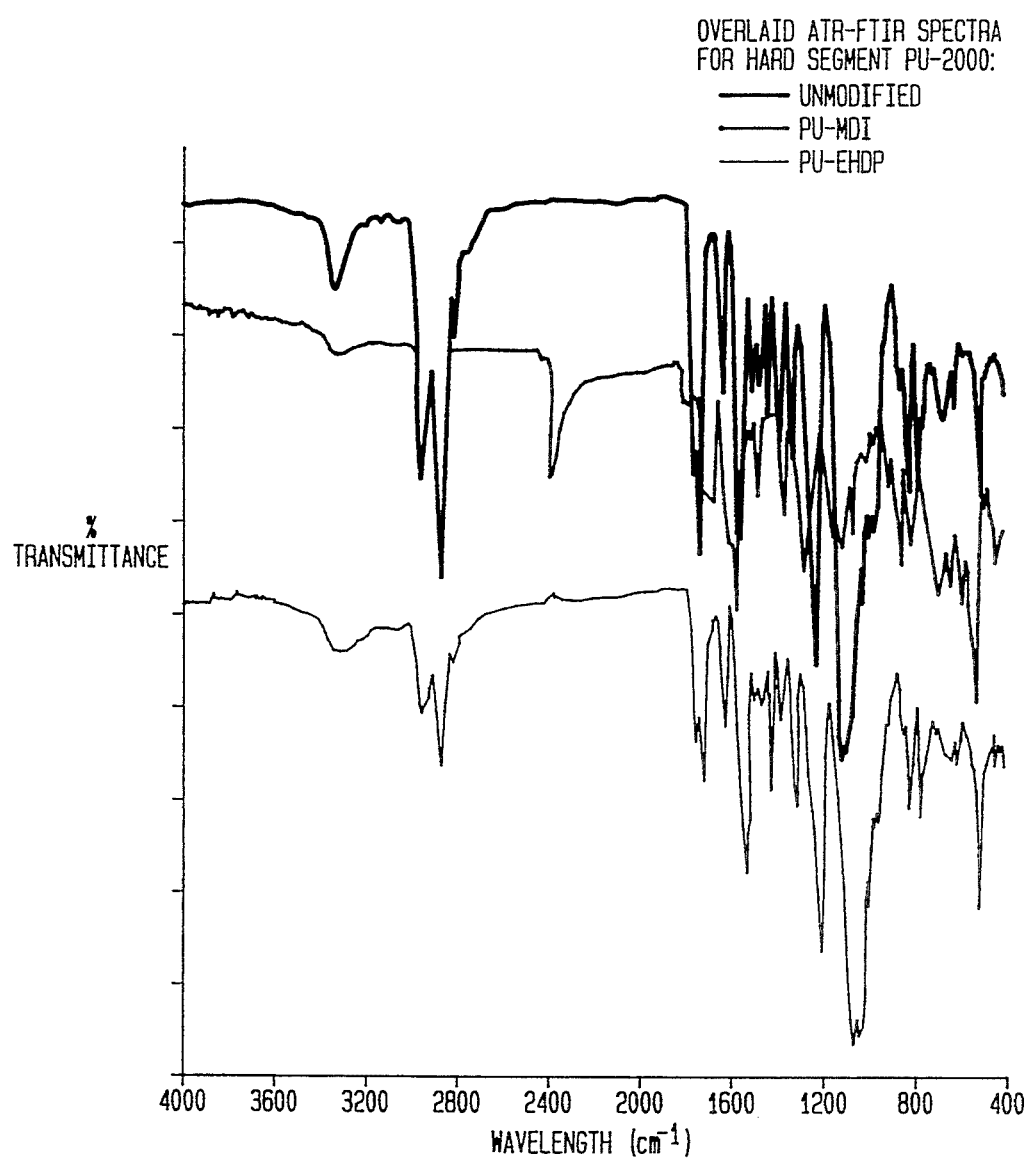
FIG. 10 is a graphical representation of the overlaid ATR-FTIR spectra of polyurethane (PU-2000), the intermediate (PU-MDI) and EHDP-containing, surface-modified polyurethane (FIG. 9, Compound 93).

ATR-FTIR spectra for PU-2000 control, the intermediate and EHDP-containing, surface-modified PU-2000 is shown in FIG. 10. The formation of the MDI-PU allophanate linkage with free isocyanate functional group is confirmed by the presence of a peak at 2410 cm. Changes in amide I and II peaks clearly demonstrate the binding of MDI through the secondary amine of the PU-2000 polymer chain. Also, the decrease in hydrogen bonding, as evident from the carbonyl bonded and non-bonded peaks confirm the binding of the MDI spacer group to the polymer. The intensities of the corresponding hard segment peaks were found to have increased by two or three-fold. This shows that the grafting of MDI on the surface of PU-2000 was successful.

Reacting EHDP with the free functional groups of MDI present on the surface of the surface-modified specimens results in a drastic change in spectral pattern. The free isocyanate functional group, seen at 2410 cm on the spectra of FIG. 10, disappeared. This disappearance clearly indicates covalent binding of EHDP through the free isocyanate function group of the MDI spacer moiety.

The results show that soft segment concentration is low at the polyurethane surface. The disappearance of the peak intensities at 2852 $cm^{-1}$ and 2938 $cm^{-1}$ after MDI-binding signifies a $-CH_2$ stretching reduction which may be the result of the blocking action of the MDI bound to the primary amine group. In addition, other peaks are submerged which further substantiates the conclusion that the surface of the modified polyurethane has a rich hard segment concentration.

It should be noted that the pathological subdermal mineralization process in the rat closely resembles that of the human cardiovascular region, hence, the rat serves as a good animal model for the study of cardiovascular calcification, both during the induction phase and progression.

The calcification-resistant materials of the present invention are ideally suited for any body-invasive uses in which pathologic calcification is a possibility. Such uses include, vascular grafts, pacemakers, numerous other prosthetic or implanted devices, such as artificial bone and hip joints, cosmetic implants of silicone, tendon prostheses, etc.

Although the invention has been described in terms of specific embodiments and applications, persons skilled in the art can, in light of this teaching, generate additional embodiments without exceeding the scope or departing from the spirit of the claimed invention. Accordingly, it is to be understood that the drawing and description in this disclosure are proffered to facilitate comprehension of the invention, and should not be construed to limit the scope thereof.

What is claimed is:

1. A material for implantation in the interior of the body of a living being, the material comprising a biocompatible synthetic polymer which is substantially insoluble in the interior of the body of a host living being and which has irreversibly bound thereto an effective amount of an polyphosphonate anticalcification agent for rendering said biocompatible synthetic polymer resistant to in vivo pathologic calcification.

2. The material of claim 1 wherein the biocompatible synthetic polymer is selected from the group consisting of polyurethane, polydimethylsiloxane, ethylene vinyl acetate, polymethyl methacrylate, polyamide, polycarbonate, polyester, polyethylene, polypropylene, polystyrene, polyvinyl chloride, polytetrafluoroethylene, polysulfone, or cellulose acetate and copolymers thereof.

3. The material of claim 1 wherein the polyphosphonate anticalcification agent is selected from the group consisting of aminopropanehydroxydiphosphonate, ethanehydroxydiphosphonate, aminotri(methylenephosphonic acid), and diethylentriaminepenta(methylenephosphonic acid).

4. The material of claim 1 further comprising an effective amount of the anticoagulant heparin irreversibly bound to said biocompatible synthetic polymer for rendering said biocompatible synthetic polymer resistant to in vivo thrombus formation.

5. A material for implantation in the interior of the body of a living being, the material being characterized by a biocompatible synthetic polymer which is substantially insoluble in the interior of the body of a host living being and which has irreversibly bound thereto via epoxide linkages an effective amount of an anticalcification agent, the anticalcification agent having at least one functional group having an active hydrogen, for rendering said biocompatible synthetic polymer resistant to in vivo pathologic calcification.

6. The material of claim 5 wherein the anticalcification agent has an amine, amide, alcohol, or carboxylic acid functionality.

7. The material of claim 6 wherein the anticalcification agent is selected from the group consisting of polyphosphonates, sulfaminotricarballyate, alpha amino oleic acid, pyrophosphate, statherin, polylysine, and polyarginine.

8. The material of claim 5 further comprising heparin irreversibly bound thereto via epoxide linkages in an amount effective for rendering said biocompatible synthetic polymer resistant to in vivo thrombus formation.

9. The material of claim 7 wherein the anticalcification agent is a polyphosphonate, the polyphosphonate having reactive hydroxy groups on the phosphonate moieties and less reactive hydroxy groups on the alkyl, aryl, or aralkyl moiety.

10. The material of claim 9 wherein the epoxide linkage is through the reactive hydroxy groups on the phosphonate moieties.

11. The material of claim 9 wherein the epoxide linkage is through the hydroxy group on the alkane.

12. A method of making a calcification-resistant biocompatible polymeric material comprising the steps of:
   forming a monoadduct of a polyphosphonate anticalcification agent and a reactive polyfunctional epoxide;
   adding the monoadduct to a prepolymer base of a biocompatible copolymer;
   adding the second component of the biocompatible copolymer; and
   polymerizing.

13. The method of claim 12 wherein the biocompatible copolymer is a polyurethane.

14. The method of claim 13 wherein the prepolymer base is a polyol and the second component is diisocyanate.

15. The method of claim 12 wherein the polyphosphonate is selected from the group consisting of aminopropanehydroxydiphosphonate, ethanehydroxydiphosphonate, aminotri(methylenephosphonic acid), and diethylentriaminepenta(methylenephosphonic acid).

16. The method of claim 12 wherein the polyfunctional epoxide is selected from the group consisting of diglycidyl butanediol ether, ethanediol diglycidyl ether, butanediol diglycidyl ether, and polyglycerol polyglycidyl ethers.

17. A method of making a calcification-resistant polymeric material comprising the steps of:
   forming a solution of a polyphosphonate anticalcification agent and a reactive polyfunctional epoxide in a solvent;
   adding to the solution a second solution of a prepolymerized biocompatible polymer to form a mixture; and
   polymerizing the mixture.

18. The method of claim 17 wherein the polyphosphonate is selected from the group consisting of aminopropanehydroxydiphosphonate, ethanehydroxydiphosphonate, aminotri(methylenephosphonic acid), and diethylentriaminepenta(methylenephosphonic acid).

19. The method of claim 17 wherein the polyfunctional epoxide is selected from the group consisting of diglycidyl butanediol ether, ethanediol diglycidyl ether, butanediol diglycidyl ether, and polyglycerol polyglycidyl ethers.

20. A method of making a calcification-resistant polymeric material comprising the steps of:
   forming a diisocyanate-terminated prepolymer by reacting a soft segment component of a polyurethane and a hard segment component of the polyurethane;
   adding a chain extender to the diisocyanate-terminated prepolymer.

21. The method of claim 20 wherein the chain extender is a short chain diol and the product is an hydroxy-terminated polyurethane.

22. The method of claim 21 comprising the further step of reacting the hydroxy-terminated polyurethane with a polyphosphonate anticalcification agent to produce a phosphonate-terminated polyurethane.

23. The method of claim 22 wherein said step of reacting comprises the steps of:
   forming a solution of the polyphosphonate anticalcification agent and a reactive polyfunctional epoxide in a solvent;
   adding to the solution a second solution of the hydroxy-terminated anticalcification agent to form a mixture; and
   polymerizing the mixture.

24. The method of claim 20 wherein the chain extender is a polyphosphonate anticalcification agent and the product is a phosphonate-terminated polyurethane.

25. A method of making a calcification-resistant polymeric material comprising the steps of:
   forming a tetraester derivative of a polyphosphonate anticalcification agent;
   reacting the tetraester derivative of a polyphosphonate anticalcification agent and a reactive polyfunctional epoxide to form a phosphonated epoxide monoadduct;
   reacting the phosphonated epoxide monoadduct with an hydroxy-terminated polymer to form a tetraester-terminated biocompatible polymer.

26. The method of claim 25 comprising the further step of hydrolyzing the tetraester-terminated biocompatible polymer to a phosphonate-terminated biocompatible polymer.

27. The method of claim 26 wherein the step of hydrolyzing comprises reacting the tetraester-terminated biocompatible polymer with bromotrimethyl silane.

28. The method of claim 26 wherein the step of hydrolyzing comprises subjecting the tetraester-terminated biocompatible polymer to water.

29. A method of making a thromboresistant polymeric material comprising the steps of:
   forming a solution of heparin and a reactive polyfunctional epoxide to form a heparin-epoxide monoadduct;
   adding a solution of a prepolymerized biocompatible polymer to the monoadduct to form a mixture; and
   polymerizing the mixture.

30. A method of making a calcification-resistant polyurethane comprising the following steps:
   (a) preparing an isocyanate-terminated prepolymer;
   (b) reacting the isocyanate-terminated prepolymer with a chain extender to form a polyurethane base polymer having a hard segment and a soft segment;
   (c) epoxidizing the polyurethane base polymer at unsaturated double bonds of the soft segment; and
   (d) covalently binding EHDP to the epoxidized base polymer.

31. A calcification-resistant polyurethane having hard segments and soft segments characterized in that the soft segment is epoxidized at the site of unsaturated carbons and that at least some of the epoxidized sites have covalently bound thereto an anticalcification agent.

32. A method of making a calcification-resistant polyurethane comprising the following steps:
   (a) coupling a hard segment modifier to polyurethane; and
   (b) coupling a diphosphonate to the polyurethane by reaction with free isocyante functional groups.

33. The method of claim 32 wherein said hard segment modifier is a polyfunctional isocyanate.

34. The method of claim 32 wherein said diphosphonate is EHDP.

* * * * *